(12) United States Patent
Gehringer et al.

(10) Patent No.: US 9,133,093 B2
(45) Date of Patent: Sep. 15, 2015

(54) PROCESS FOR PREPARING POLYESTER ALCOHOLS

(71) Applicant: BASF SE, Ludwigshafen (DE)

(72) Inventors: Lionel Gehringer, Schaffhouse-pres-Seltz (FR); Veronika Wloka, Mannheim (DE); Ulrich Mueller, Neustadt (DE); Marine Boudou, Mannheim (DE); Ulrike Mahn, Mannheim (DE); Elke Guetlich-Hauk, Lambsheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/498,294

(22) Filed: Sep. 26, 2014

(65) Prior Publication Data

US 2015/0011792 A1    Jan. 8, 2015

Related U.S. Application Data

(63) Continuation of application No. 13/391,057, filed as application No. PCT/EP2010/061895 on Aug. 16, 2010, now abandoned.

(30) Foreign Application Priority Data

Aug. 20, 2009   (EP) .................... 09168315

(51) Int. Cl.
| | |
|---|---|
| *C07C 67/08* | (2006.01) |
| *C08G 18/42* | (2006.01) |
| *C08G 63/06* | (2006.01) |
| *C08G 63/12* | (2006.01) |
| *C08G 63/82* | (2006.01) |
| *C08G 63/87* | (2006.01) |
| *B01J 29/89* | (2006.01) |

(52) U.S. Cl.
CPC ................. *C07C 67/08* (2013.01); *B01J 29/89* (2013.01); *C08G 18/4238* (2013.01); *C08G 63/06* (2013.01); *C08G 63/12* (2013.01); *C08G 63/823* (2013.01); *C08G 63/87* (2013.01)

(58) Field of Classification Search
CPC .... C08G 18/4238; C08G 63/06; C08G 63/12; C08G 63/87; C08G 63/823; C07C 67/08; B01J 29/89
USPC .................................. 528/271, 272, 275, 279
See application file for complete search history.

(56) References Cited

U.S. PATENT DOCUMENTS

| | | | |
|---|---|---|---|
| 5,143,984 | A | 9/1992 | Jenkins et al. |
| 5,187,216 | A | 2/1993 | Cassell et al. |
| 5,733,969 | A | 3/1998 | Thiele |
| 5,952,455 | A | 9/1999 | Yanagisawa et al. |
| 6,740,616 | B2 | 5/2004 | Muller et al. |
| 2006/0036054 | A1 | 2/2006 | Upshaw et al. |

FOREIGN PATENT DOCUMENTS

| | | |
|---|---|---|
| EP | 0 311 983 | 4/1989 |
| EP | 0 405 978 | 1/1991 |
| WO | 2006 100231 | 9/2006 |
| WO | 2010 035579 | 4/2010 |

OTHER PUBLICATIONS

International Search Report Issued Oct. 7, 2010 in PCT/EP10/61895 Filed Aug. 16, 2010.

*Primary Examiner* — Frances Tischler
(74) *Attorney, Agent, or Firm* — Oblon, McClelland, Maier & Neustadt, L.L.P.

(57) ABSTRACT

The invention relates to a process for preparing polyester alcohols by catalytic reaction of at least one at least polyfunctional carboxylic acid with at least one polyfunctional alcohol and/or by catalytic ring-opening polymerization of cyclic esters in the presence of catalysts, wherein a zeolite is used as catalyst.

4 Claims, No Drawings

PROCESS FOR PREPARING POLYESTER ALCOHOLS

CONTINUING APPLICATION INFORMATION

This application is a Continuation of U.S. application Ser. No. 13/391,057, filed on Feb. 17, 2012, now pending.

The invention relates to a process for preparing polyester alcohols and also to the use of these polyester alcohols for producing polyurethanes.

The preparation of polyester alcohols and the use of such products in polyurethane chemistry have been known for a long time and been widely described. These products are usually prepared by polycondensation reactions of polybasic carboxylic acids and/or carboxylic acid derivatives with polyhydric alcohols or polyols. Mention may be made by way of example of Kunststoffhandbuch, volume VII, Polyurethane, Carl-Hanser-Verlag, Munich $1^{st}$ edition 1966, edited by Dr. R Vieweg and Dr. A. Höchtlen, and also $2^{nd}$ edition 1983 and the $3^{rd}$ revised edition 1993, edited by Dr. G. Oertel. It is also known that polyester alcohols can be prepared by polycondensation reactions of ω-hydroxycarboxylic acid or by ring-opening polymerization of cyclic esters, known as lactones.

However, it is also possible to process polyester scrap and in particular polyethylene terephthalate (PET) or polybutylene terephthalate (PBT) scrap. A whole range of processes is known and has been described for this purpose. The basis of some processes is the conversion of the polyester into a diester of terephthalic acid, e.g. dimethyl terephthalate. DE-A 1003714 and U.S. Pat. No. 5,051,528 describe such transesterifications using methanol and transesterification catalysts.

The use of these polyester alcohols for, in particular, producing polyurethanes, hereinafter also referred to as PURs, in particular flexible PUR foam, rigid PUR foam and other cellular or noncellular PUR materials requires a specific choice of starting materials and the polycondensation technology to be carried out. To produce polyurethane, it is particularly important that the polyester alcohols used have a low acid number (see Ullmann's Encyclopedia, Electronic Release, Wiley-VCH-Verlag GmbH, Weinheim, 2000 under the keyword "polyesters", paragraph 2.3 "Quality Specifications and Testing"). The acid number should be as small as possible since the terminal acid groups react more slowly with diisocyanates than do terminal hydroxyl groups. Polyester alcohols having high acid numbers therefore lead to a lower molecular weight buildup during the reaction of polyester alcohols with isocyanates to form polyurethane.

A further problem with the use of polyester alcohols having high acid numbers for the polyurethane reaction is that amide formation with liberation of carbon dioxide occurs in the reaction of the numerous terminal acid groups with isocyanates. The gaseous carbon dioxide can then lead to undesirable bubble formation. Furthermore, free carboxyl groups impair the catalysis in the polyurethane reaction and also the stability of the resulting polyurethanes to hydrolysis.

The known polycondensation technology for preparing polyester alcohols is the use of polyfunctional aromatic and/or aliphatic carboxylic acids or anhydrides thereof and bifunctional, trifunctional and/or higher-functional alcohols, in particular glycols, which are reacted with one another at temperatures of, in particular, 150-280° C. under atmospheric pressure and/or a slight vacuum in the presence of catalysts with removal of the water of reaction. The customary technology is described, for example, in DE-A-2904184 and comprises combining the reaction components at the beginning of the synthesis with a suitable catalyst while simultaneously increasing the temperature and reducing the pressure. The temperatures and the reduced pressure are then changed further during the course of the synthesis. The polycondensation reactions can be carried out either in the presence or absence of a solvent.

A disadvantage is the fact that by-products are frequently formed in the poly-condensation reaction at high temperatures. Furthermore, the high-temperature polycondensations have to take place with exclusion of water in order to avoid the reverse reaction. This is generally achieved by carrying out the condensation under reduced pressure, under an inert gas atmosphere or in the presence of an entrainer gas to effect complete removal of the water.

A further disadvantage of these polycondensations at high temperatures is that they proceed relatively slowly. To accelerate the polycondensation reaction at high temperatures, esterification catalysts are therefore frequently used. Classical esterification catalysts employed are, for example, iron, cadmium, cobalt, lead, zinc, zirconium, hafnium, aluminum, antimony, magnesium, titanium and tin catalysts in the form of metals, metal oxides or metal salts, or acids, e.g. sulfuric acid, p-toluenesulfonic acid, or bases, e.g. potassium hydroxide or sodium methoxide.

These esterification catalysts are homogeneous and generally remain in the polyester alcohol after completion of the reaction. A disadvantage here is that the esterification catalysts remaining in the polyester alcohol may interfere in the resistance of the polyester alcohols produced to hydrolysis and also in the later conversion of these polyester alcohols into the polyurethane.

Furthermore, the presence of the homogeneous catalysts in the polyester alcohol can lead to discoloration.

To overcome this disadvantage, WO 2006/100231 describes a process for preparing polyester alcohols in which enzymes are used as catalysts. The preparation or transesterification of polyester alcohols by means of enzymes can be carried out batchwise or continuously. In the continuous process, the catalyst is preferably present in immobilized form, with the reaction preferably being carried out in a flow reactor.

However, the high-temperature polycondensations and the enzymatically catalyzed polycondensations for preparing polyester alcohols both have the disadvantage that the preparation of polyester alcohols is carried out by means of condensation reactions in plants for which a complicated periphery is necessary. The classical high-temperature polycondensation and also the enzymatic polycondensation require facilities on the reactor for the metered addition of liquids and/or solids. Water has to be removed from the reaction mixture under reduced pressure, by introduction of an inert gas or by means of an entrainer distillation. In addition, the water has to be separated off from the diols by distillation, since these have to remain in the reaction mixture as reaction partners for the acid component. The separation of water and diols is generally effected by means of a distillation column. Apparatuses for generating reduced pressure, e.g. pumps, for separating diols and water, e.g. distillation columns, or for introducing an inert gas stream incur high capital costs. In addition, particularly in the case of the high-temperature condensation, facilities for producing temperatures inside the reactor of 160-270° C. are necessary.

Disadvantages of enzymatic catalysts are their high price and the adverse effect on the odor and the color of the resulting polyester alcohols. Furthermore, detachment of the enzymes from their support can occur.

DE 10 2008 004 343 describes a process for preparing polyester alcohols, in which multimetal cyanide catalysts, also referred to as DMC catalysts, are used as heterogeneous catalysts. Such catalysts are known and are frequently used as catalysts for preparing polyether alcohols by addition of alkylene oxides onto compounds having reactive hydrogen atoms. In the preparation of polyester alcohols, it has been found that DMC catalysts are not very suitable since their catalytic activity is unsatisfactory and no homogeneous products are obtained.

EP 1679322 describes a process for preparing polyesters by reacting polyfunctional alcohols with polyfunctional carboxylic acids. Metal silicates are used as catalysts. The products described in this document are not polyester alcohols but rather thermoplastic products. The use of the catalysts mentioned is said to make the preparation of products having a very high molecular weight easier. Furthermore, the behavior in the thermoplastic processing of the products and the mechanical properties of the end products are said to be improved; in particular, the tendency for the products to be thermally degraded during processing is said to be reduced.

It was an object of the present invention to develop a process for the catalytic preparation of polyester alcohols using heterogeneous catalysts, which is simple and inexpensive. The process should lead to colorless and catalyst-free products which can be used without complicated work-up for producing polyurethanes. Furthermore, it should also be possible to use the catalyst as a fixed bed.

The object has surprisingly been able to be achieved by using a zeolite as catalyst for the preparation of the polyester alcohols.

The invention accordingly provides a process for preparing polyester alcohols by catalytic reaction of at least one polyfunctional carboxylic acid with at least one polyfunctional alcohol and/or by catalytic ring-opening polymerization of cyclic esters, preferably lactones, in particular ε-caprolactone, in the presence of catalysts, wherein a zeolite is used as catalyst.

In an embodiment of the process of the invention, the entire reaction of the monomers to form the polyester alcohol is carried out using zeolites.

However, it is also possible to carry out only part of the reaction using zeolites. The remaining part of the reaction can be carried out in the absence of catalysts or using other esterification catalysts.

Zeolites are, as is known, crystalline aluminosilicates having ordered channel and cage structures whose pore openings are in the micropore range. According to IUPAC, micropores are pores whose diameters are smaller than 2 nm. The framework of such zeolites is made up of $SiO_4$ and $AlO_4$ tetrahedra which are joined via common oxygen bridges. In an analogous way, there are aluminophosphates made up of $PO_4$ and $AlO_4$ tetrahedra, known as AlPOs, MeAPOs, MeAPSOs having a structure analogous to zeolites, and likewise metal imidazolates, known as ZIFs, having a structure analogous to zeolites. These materials which are analogous to zeolites are all included within the scope of the present invention. An overview of known structures may be found, for example, in Ch. Baerlocher, W. M. Meier, D. H. Olson, "Atlas of Zeolite Framework Types", 5th ed. Elsevier, 2001.

Zeolites which do not comprise any aluminum and in which titanium as Ti(IV) partly replaces the Si(IV) in the silicate lattice are also known. These titanium zeolites, in particular those having a crystal structure of the MFI type, and possible ways of preparing them are described, for example, in EP-A 311 983 or EP-A 405 978. Apart from silicon and titanium, such materials can also comprise additional elements such as aluminum, zirconium, germanium, tin, iron, cobalt, nickel, gallium, boron or small amounts of fluorine.

As zeolites, preference is given to using ones comprising titanium, hereinafter referred to as titanium zeolites. The term titanium zeolite thus refers to a material which comprises small amounts of titanium in addition to silicon oxide and incorporated in a zeolite structure.

Preferred titanium zeolites are those having pentasil units in the structure, e.g. MFI, MEL, BEA, MOR, MWW structure, in particular the types which can be assigned X-ray-crystallographically to the MFI, MOR, BEA, MWW, RRO, LEV, FER structure, in particular to the MFI structure, MEL structure or MFI/MEL mixed structure. Zeolites of this type are described, for example, in "Atlas of Zeolite Framework Types", Ch. Baerlocher, W. M. Meier, D. H. Olson, 5th ed. Elsevier, 2001.

The titanium zeolites mentioned are usually prepared by reacting an aqueous mixture of an $SiO_2$ source, a titanium source such as titanium dioxide or titanium alkoxide and a nitrogen-comprising organic template for forming this structure, e.g. tetrapropylammonium hydroxide, optionally with addition of alkali metal compounds, in a pressure vessel at elevated temperature for a period ranging from a few hours to some days, forming the crystalline product. This is separated off, e.g. filtered off, washed, dried and calcined at elevated temperature to remove the organic nitrogen base. In the catalysts according to the invention for preparing polyester alcohols, the molar ratio of titanium to the sum of silicon plus titanium is generally in the range from 0.01:1 to 0.1:1. In the powder obtained in this way, the titanium is at least partly present in alternate four-fold, five-fold or six-fold coordination within the zeolite framework. It is known that titanium zeolites having the MFI structure can be identified by a particular X-ray diffraction pattern and also by a framework vibration band in the infrared (IR) region at about 960 $cm^{-1}$ and thus differ from alkali metal titanates or crystalline and amorphous $TiO_2$ phases.

The titanium zeolites prepared in this way can be used in the form of powders, spray-dried agglomerates or shaped bodies such as extrudates, crushed material, rings, hollow cylinders, spheres or pellets. As shaping process, it is in principle possible to use all methods for appropriate shaping as are generally customary for catalysts. Preference is given to processes in which shaping is effected by extrusion in customary extruders, for example to form extrudates having a diameter of usually from 1 to 10 mm, in particular from 2 to 5 mm. If binders and/or auxiliaries are required, a mixing or kneading process advantageously precedes extrusion. If appropriate, a calcination step is carried out after extrusion. The extrudates obtained are optionally comminuted, preferably to form granules or crushed material having a particle diameter of from 0.1 to 5 mm, in particular from 0.5 to 2 mm.

Suitable binders are in principle all compounds used for such purposes; preference is given to compounds, in particular oxides, of silicon, aluminum, boron, phosphorus, zirconium and/or titanium or else clays, e.g. montmorillonites, kaolins or bentonites or other zeolites. Silicon dioxide, which can be introduced as silica sol or in the form of tetraalkoxysilanes in the shaping step, is of particular interest as binder. As auxiliaries for the consolidating shaping processes, mention may be made by way of example of extrusion aids; a customary extrusion aid is methylcellulose. Such agents are generally completely burnt in a subsequent calcination step.

The catalysts processed to form shaped bodies comprise up to 50% by weight of binder, based on the total mass of the catalyst, with preferred binder contents being from 0.1 to 30% by weight, particularly preferably from 2 to 25% by weight.

The catalysts are generally activated by means of elevated temperature, preferably from 100 to 800° C., particularly preferably from 200 to 600° C., and other conditions known to those skilled in the art before use. In many cases, the catalysts can be regenerated by reaction with air, lean air, i.e. a mixture of nitrogen and oxygen having a proportion of oxygen which is less than that of air, or by extraction or rinsing with organic solvents or water.

When used as powder, the catalysts are preferably used in an amount of from 0.001 to 1% by weight, based on the weight of the polyester alcohol. The amount of catalyst is preferably in the range from 0.15 to 0.25% by weight, based on the weight of the polyester alcohol.

After the reaction, the catalyst is removed from the product. This is preferably carried out by means of filtration.

After purification, the polyester alcohol usually comprises less than 1 ppm of titanium and less than 100 ppm of silicon, preferably less than 0.5 ppm of titanium and 50 ppm of silicon, particularly preferably less than 0.2 ppm of titanium and 20 ppm of silicon, and in particular less than 0.1 ppm of titanium and 10 ppm of silicon.

The catalyst which has separated off can be reused for the process. Here, it can be freed of adhering polyester alcohol before reuse.

In principle, the catalyst could also be left in the polyester alcohol but this is not preferred since it can lead to problems in the further processing to form polyurethanes, in particular thermoplastic polyurethanes (TPUs).

The conversion of the starting materials into the polyester alcohol in the presence of the catalysts described is carried out under the conditions customary for this purpose.

The preparation of the polyester alcohols is, as described, preferably carried out by reaction of polyfunctional carboxylic acids with polyfunctional alcohols.

The preparation of the polyester alcohols can be carried out in one or two stages. In the single-stage process, the esterification of the carboxylic acids and alcohols is carried out during the entire reaction and the finished polyester alcohol is then taken off. In the two-stage reaction, a polyester alcohol is prepared in a first stage a) and this is reacted with further carboxylic acids and alcohols or with a polyester alcohol in a second stage b).

The entire reaction or part of the reaction can be carried out using zeolite catalysts. In the two-stage reaction, one stage can be carried out using a zeolite catalyst and the other can be carried out using another catalyst. If this procedure is employed, the second stage is preferably carried out using a zeolite catalyst.

The polyester alcohols prepared by the process of the invention have, depending on the desired application, a hydroxyl number in the range from 20 to 400 mg KOH/g. The hydroxyl number of polyester alcohols used for producing flexible polyurethane foams and cellular or thermoplastic polyurethane elastomers is preferably in the range from 20 to 250 mg KOH/g. Polyester alcohols for use in rigid polyurethane foams preferably have a hydroxyl number above 100 mg KOH/g, in particular in the range from 100 to 400 mg KOH/g.

As polyfunctional carboxylic acids, use is usually made of dicarboxylic acids such as aliphatic dicarboxylic acids, preferably succinic acid, glutaric acid, adipic acid, suberic acid, azelaic acid, sebacic acid, decanedicarboxylic acid, maleic acid fumaric acid, or other aliphatic dicarboxylic acids, or aromatic dicarboxylic acids such as phthalic acid, isophthalic acid or terephthalic acid. The dicarboxylic acids can be used either individually or in admixture with one another. In place of or in admixture with the dicarboxylic acids, it is also possible to use the corresponding dicarboxylic acid derivatives, e.g. dicarboxylic esters of alcohols having from 1 to 4 carbon atoms or anhydrides thereof, for example phthalic anhydride.

Suitable polyhydroxyl compounds are all at least dihydric alcohols, but preferably diol components such as ethylene glycol, diethylene glycol, 1,3-propanediol, 1,2-propanediol, dipropylene glycol, 1,4-butanediol, 1,5-pentanediol, 1,6-hexanediol, 1,10-decanediol, neopentyl glycol, 2-methyl-1,3-propanediol, 3-methyl-1,5-pentanediol. To increase the functionality of the polyester alcohols, trifunctional or higher-functional alcohols can also be used. Examples of such alcohols are glycerol, trimethylolpropane and pentaerythritol. It is also possible to use oligomeric or polymeric products having at least two hydroxyl groups. Examples of such products are polytetrahydrofuran, polylactones, polyglycerol, polyetherols, polyesterol or $\alpha$-$\omega$-dihydroxypolybutadiene.

To prepare the polyester alcohols, the organic polycarboxylic acids and/or derivatives and polyhydric alcohols are preferably polycondensed in a molar ratio of 1:1-2.1, preferably 1:1.05-1.9.

The single-stage preparation of the polyester alcohols or reaction step a) of the two-stage preparation of the polyester alcohols is, as described, carried out by reaction of the polyfunctional carboxylic acids with the polyfunctional alcohols with removal of water. Process step a) is preferably carried out using a stirred tank reactor provided with agitator and distillation column. This apparatus is generally a closed system and can generally be evacuated by means of a vacuum pump. The starting materials are heated while stirring and preferably with exclusion of air (e.g. in a nitrogen atmosphere or under reduced pressure). The water formed in the polycondensation is preferably distilled off at a low pressure or a continuously decreasing pressure (see Batchwise Vacuum-Melt-Verfahren, Houben-Weyl 14/2, 2).

The reaction temperature is preferably in the range from 160 to 280° C. The pressure is gradually reduced during the course of the reaction, and the final pressure is preferably below 200 mbar. At this pressure, the reaction is continued to the desired degree of conversion.

In a single-stage process, the entire reaction can preferably be carried out using zeolite catalysts. It is also possible to use different catalysts during the course of the reaction, but this embodiment is not preferred. The polyester alcohols prepared by the single-stage process usually have the above-described hydroxyl numbers and acid numbers of less than 2 mg KOH/g.

In the two-stage preparation of the polyester alcohols, the reaction products of step a) preferably have a number average molecular weight in the range from 200 g/mol to 10 000 g/mol, particularly preferably in the range 500-5000 g/mol.

The acid numbers of the base polyester alcohols prepared in step a) are preferably less than 10 g KOH/kg, more preferably less than 5 g KOH/kg, in particular less than 2 g KOH/kg. The acid number serves as a measure of the content of free organic acids in the polyesterol. The acid number is determined by the number of mg of KOH (or g of KOH) consumed in the neutralization of 1 g (or 1 kg) of the sample.

The functionality of the base polyester alcohols prepared in step a) is, depending on the raw materials used, preferably in the range from ≥1.9 to 4.0, more preferably in the range from 2.0 to 3.0.

As described, step a) can be carried out using zeolite catalysts. However, it is also possible to work without catalysts or preferably using customary esterification catalysts. Examples of customary esterification catalysts are preferably metal-organic compounds such as titanium tetrabutoxide, tin dioctoate or dibutyltin dilaurate, an acid such as sulfuric acid, p-toluenesulfonic acid or a base such as potassium hydroxide or sodium methoxide. These esterification catalysts are generally homogeneous and generally remain in the polyester alcohol after completion of the reaction. The reaction is carried out at 160-280° C., preferably 200-260° C.

The second process step (step b)) of the two-stage process is preferably carried out exclusively by means of zeolite catalysts. The reaction carried out in step b) is either 1. transesterification catalyzed by means of zeolite catalysts without additional glycolysis,
2. glycolysis catalyzed by means of zeolite catalysts without additional transesterification or
3. a mixed reaction comprising transesterification catalyzed by means of zeolite catalysts and glycolysis or alcoholysis catalyzed by means of zeolite catalysts.

In the transesterification catalyzed by means of zeolite catalysts, (see No. 1), two or more base polyester alcohols from step a) are admixed with a sufficient amount of zeolite catalysts, but in this case no additional polyfunctional polyhydroxy compound (diols, glycols) is added. This leads to formation of a new polyesterol which in the ideal case is a random copolymer of the monomers of all base polyester alcohols used.

In the glycolysis catalyzed by means of zeolite catalysts, only one base polyester alcohol from step a) is reacted with one or more polyhydroxy compounds, preferably diols or polyols, and a suitable amount of zeolite catalyst. In this case, the mean molecular weight of the base polyester alcohol is generally reduced by glycolysis or by alcoholysis of part of the ester bonds.

As an alternative, a mixed reaction comprising a transesterification catalyzed by means of zeolite catalysts and a glycolysis or alcoholysis catalyzed by means of zeolite catalysts can also take place in process step b). Here, a mixture of at least two base polyester alcohols from step a) and at least one polyfunctional polyhydroxy compound, preferably diols or polyols, with a suitable amount of the zeolite catalyst is reacted. The change in the mean molecular weight or in the other materials parameters of the base polyester alcohols, e.g. viscosity, acid number or melting point, in this variant of process step b) depends on the components used in the particular case, in particular on the type and amount of the base polyester alcohols used and on the type and amount of the polyhydroxy compounds used.

The properties of the end product from step b) likewise depend on whether the transesterification or glycolysis according to step b) has proceeded to completion. The completeness of the transesterification or glycolysis according to step b) in turn depends on the reaction time, with long reaction times resulting in complete transesterification or glycolysis. The reaction times for the transesterification step b) are preferably chosen so that the polyester alcohols finally obtained have very similar properties to polyester alcohols prepared by the classical single-stage high-temperature polycondensation process. The reaction time for the transesterification or glycolysis according to step b) can be from 1 to 36 hours, preferably from 2 to 24 hours.

The reaction in process step b) can, like that in process step a), be carried out in the presence of a solvent or in the absence of a solvent (reaction "in bulk").

If the reaction in process step b) is carried out in the presence of a solvent, it is possible to use all known suitable solvents, in particular the solvents toluene, dioxane, hexane, tetrahydrofuran, cyclohexane, xylene, dimethyl sulfoxide, dimethylformamide, N-methylpyrrolidone, chloroform. The choice of solvent depends in the particular case on the starting materials used, (the base polyester alcohols and the polyhydroxy compounds) and in particular on their solubility properties. However, the reaction of process step b) in the presence of a solvent has the disadvantage that it comprises additional process substeps, namely dissolution of the at least one base polyester alcohol in the solvent and removal of the solvent after the reaction. Furthermore, the dissolution of the at least one base polyester alcohol in the solvent can, depending on the hydrophobicity of the base polyester alcohol, be problematical and may decrease the yield.

In a further preferred embodiment of the process, process step b) is preferably carried out using base polyester alcohols and, if appropriate, additional polyhydroxyl compounds which together have a water content of less than 0.1% by weight, preferably less than 0.05% by weight, more preferably less than 0.03% by weight, in particular less than 0.01% by weight. At higher water contents during process step b), hydrolysis also takes place in addition to the transesterification, so that the acid number of the polyester alcohol would increase in an undesirable way during step b). Carrying out step b) of the process of the invention at a water content of less than 0.1% by weight, preferably less than 0.05% by weight, more preferably less than 0.03% by weight, in particular less than 0.01% by weight, thus leads to the formation of specialty polyester alcohols having a low acid number as end products. Polyester alcohols having a low acid number are generally more stable to hydrolysis than polyester alcohols having a high acid number, since free acid groups catalyze the reverse reaction, i.e. hydrolysis.

Preparation of polyester alcohols having water contents of more than 0.1% by weight leads to polyester alcohols having an acid number of greater than 10 mg KOH/g. However, polyester alcohols having such high acid numbers (greater than 10 mg KOH/g) are unsuitable or have only limited suitability for most industrial applications, in particular for use in the production of polyester alcohols.

Polyester alcohols also take up, depending on atmospheric humidity and temperature, at least 0.01% by weight, but in general at least 0.02% by weight, in some cases even more than 0.05% by weight, of water. Depending on the degree of conversion and the molecular weight of the base polyester alcohols used, this water concentration is higher than the equilibrium water concentration. If the polyester alcohol is not dried before process step b), hydrolysis of the polyester alcohol inevitably occurs.

The water content of the base polyester alcohols used in step b) is therefore preferably reduced by drying before the transesterification in process step b). Any polyfunctional polyhydroxyl compound to be used, for example the diol, is preferably also dried before the transesterification reaction in order to attain the abovementioned low water content in the transesterification. Drying can be carried out by means of customary drying methods known from the prior art, for example by drying over molecular sieves or by means of falling film evaporators. As an alternative, base polyester alcohols having low water contents, preferably less than 0.1% by weight, more preferably less than 0.05% by weight, more preferably less than 0.03% by weight, in particular less than 0.01% by weight, can also be obtained by carrying out the reaction according to process step a) and any temporary storage of the at least one base polyester alcohol entirely under inert conditions, for example in an inert gas atmosphere, preferably in a nitrogen atmosphere. In this case, the base polyester alcohols have, from the beginning, no opportunity of taking up relatively large amounts of water from the environment. A separate drying step could then become superfluous.

In a further preferred embodiment of the process, the at least one base polyester alcohol from process step a) is therefore temporarily stored, preferably in an inert gas atmosphere, so as to keep the water content low before the reaction in process step b). A mixture of two or more base polyester alcohols can then be put together from the temporarily stored base polyester alcohols in suitable ratios in order to obtain a particular specialty polyester alcohol having very specific physical properties and a specific structure after the transesterification and after any additional glycolysis by means of polyhydroxy compounds.

The polyester alcohols prepared by the two-stage process of the invention generally have relatively low acid numbers, viz. preferably acid numbers of less than 3 mg of KOH per gram of polyesterol, more preferably less than 2 mg of KOH per gram of polyester alcohol, in particular less than 1 mg of KOH per gram of polyester alcohol.

These low acid numbers are ensured by, in particular, process step b) preferably being carried out at a water content of less than 0.1% by weight, more preferably less than 0.05% by weight, more preferably less than 0.03% by weight, in particular less than 0.01% by weight.

As described above, the polyester alcohols can also be prepared by ring-opening polymerization of cyclic esters, preferably lactones, in particular ε-caprolactone. These cyclic esters can be used either alone or in admixture with the above-described starting materials.

To carry out process step a), it is possible to use all reactors whose use is known for classical high-temperature polycondensations (see Ullmann Encyclopedia (Electronic Release), chapter: Polyesters, paragraph: Polyesters as Intermediates for Polyurethane).

Process step b) is usually carried out in a temperature range of 50-160° C., preferably under atmospheric pressure. The reaction is preferably carried out in an inert atmosphere with exclusion of moisture, for example by passing nitrogen over the reaction mixture. Process step b) is preferably carried out in a heated stirred tank or fixed-bed reactor. The process of the invention can be carried out batchwise, semicontinuously or continuously.

The polyester alcohols prepared by the process of the invention can preferably be processed by reaction with isocyanates to form polyurethanes, e.g. rigid polyurethane foams, flexible polyurethane foams, integral foams, for example shoe soles. A particularly preferred field of use is the production of thermoplastic polyurethane elastomers, also referred to as TPUs.

Processes for producing the polyurethanes are likewise generally known. For example, thermoplastic polyurethanes can be produced by reacting diisocyanates with compounds having at least two hydrogen atoms which are reactive toward isocyanate groups, preferably bifunctional alcohols and, if appropriate, chain extenders having a molecular weight of from 50 to 499, in the presence or absence of catalysts and/or customary auxiliaries.

As diisocyanates, it is possible to use customary aromatic, aliphatic, cycloaliphatic and/or araliphatic isocyanates, preferably diisocyanates, for example diphenylmethane 2,2'-, 2,4'- and/or 4,4'-diisocyanate (MDI), naphthylene 1,5-diisocyanate (NDI), tolylene 2,4- and/or 2,6-diisocyanate (TDI), diphenylmethane diisocyanate, 3,3'-dimethyl-biphenyl diisocyanate, 1,2-diphenylethane diisocyanate and/or phenylene diisocyanate, trimethylene, tetramethylene, pentamethylene, hexamethylene, heptamethylene and/or octamethylene diisocyanate, 2-methylpentamethylene 1,5-diisocyanate, 2-ethyl-butylene 1,4-diisocyanate, pentamethylene 1,5-diisocyanate, butylene 1,4-diisocyanate, 1-isocyanato-3,3,5-trimethyl-5-isocyanatomethylcyclohexane (isophorone diisocyanate, IPDI), 1-methylcyclohexane 2,4- and/or 2,6-diisocyanate, dicyclohexylmethane 4,4'-, 2,4'- and/or 2,2'-diisocyanate (H12MDI), 2,6-diisocyanato-hexanecarboxylic esters, 1,4- and/or 1,3-bis(isocyanatomethyl)cyclohexane (HXDI), cyclohexane 1,4-diisocyanate, 1-methylcyclohexane 2,4- and/or 2,6-diisocyanate and/or dicyclohexylmethane 4,4'-, 2,4'- and 2,2'-diisocyanate, preferably diphenylmethane 2,2'-, 2,4'- and/or 4,4'-diisocyanate (MDI), naphthylene 1,5-diisocyanate (NDI), tolylene 2,4- and/or 2,6-diisocyanate (TDI), hexamethylene diisocyanate, dicyclohexylmethane 4,4'-, 2,4'- and/or 2,2'-diisocyanate (H12MDI), and/or IPDI, in particular 4,4'-MDI and/or hexamethylene diisocyanate and/or H12MDI.

As compounds which are reactive toward isocyanates, use is made of, as described above, the polyester alcohols of the invention. In admixture with these, it is possible to use generally known compounds which are reactive toward isocyanates, for example polyesterols, polyetherols and/or polycarbonate diols, which are usually summarized under the term "polyols", having molecular weights of from 500 to 12 000 g/mol, preferably from 600 to 6000 g/mol, in particular from 800 to 4000 g/mol, and preferably an average functionality of from 1.8 to 2.3, preferably from 1.9 to 2.2, in particular 2. Preference is given to using exclusively the polyester alcohols of the invention as compounds which are reactive toward isocyanates.

Compounds which are reactive toward isocyanates also include chain extenders. As chain extenders, it is possible to use generally known aliphatic, araliphatic, aromatic and/or cycloaliphatic compounds having a molecular weight of from 50 to 499, preferably 2-functional compounds, for example alkanediols having from 2 to 10 carbon atoms in the alkylene radical, preferably 1,4-butanediol, 1,6-hexanediol, 1,3-propanediol, 1,2-ethylene glycol and/or dialkylene, trialkylene, tetraalkylene, pentaalkylene, hexaalkylene, heptaalkylene, octaalkylene, nonaalkylene and/or decaalkylene glycols having from 3 to 8 carbon atoms, preferably unbranched alkanediols, in particular 1,3-propanediol, 1,4-butanediol and 1,6-hexanediol.

Catalysts which accelerate the reaction between the NCO groups of the diisocyanates and the hydroxyl groups of formative components are usually used. These are the customary tertiary amines known from the prior art, e.g. triethylamine, dimethylcyclohexylamine, N-methylmorpholine, N,N'-dimethylpiperazine, 2-(dimethyl-aminoethoxy)ethanol, diazabicyclo[2.2.2]octane and the like and in particular organic metal compounds such as titanic esters, iron compounds such as iron(III) acetylacetonate, tin compounds, e.g. tin diacetate, tin dioctoate, tin dilaurate or the dialkyltin salts of aliphatic carboxylic acids, e.g. dibutyltin diacetate, dibutyltin dilaurate or the like. The catalysts are usually used in amounts of from 0.00001 to 0.1 part by weight per 100 parts by weight of polyhydroxyl compound.

Apart from catalysts, customary auxiliaries can also be added to the formative components. Examples which may be mentioned are surface-active substances, flame retardants, nucleating agents, lubricants and mold release agents, dyes and pigments, inhibitors, stabilizers against hydrolysis, light, heat, oxidation or discoloration, protective agents against microbial degradation, inorganic and/or organic fillers, reinforcing materials and plasticizers.

Further details regarding the abovementioned auxiliaries and additives may be found in the specialist literature, e.g. Plastics Additive Handbook, 5th edition, H. Zweifel, ed, Hanser Publishers, Munich, 2001. All molecular weights mentioned in this text have the unit [g/mol].

To adjust the hardness of the TPUs, the formative components polyols and chain extenders can be varied within a relatively wide molar ratio range. Molar ratios of polyols to the total chain extenders to be used of from 10:1 to 1:10, in particular from 1:1 to 1:4, have been found to be useful, with the hardness of the TPUs increasing with increasing content of chain extenders.

The production of the polyurethanes can be carried out batchwise or continuously by known methods, for example using reaction extruders or the belt process by means of the one-shot or prepolymer process, preferably by the one-shot process. In the prepolymer process, the components isocyanates, polyols and, if appropriate, chain extenders, catalysts and/or auxiliaries to be reacted can be mixed with one another either in succession or simultaneously, with the reaction commencing immediately. In the extruder process, the formative components isocyanates, polyols and, if appropriate, chain extenders, catalysts and/or auxiliaries are introduced individually or as a mixture into the extruder and reacted at temperatures of usually from 100° C. to 280° C., preferably from 140° C. to 250° C. The TPU obtained is extruded, cooled and pelletized.

The process of the invention has surprisingly made it possible to reduce the reaction time required for preparing the polyester alcohols. The polyester alcohols display improved storage stability and a low color number. There were no disadvantages in the processing properties and in the characteristic properties of the polyurethanes produced using the polyester alcohols.

The invention is illustrated by the following examples.

EXAMPLE 1

Production of a Zeolite Extrudate 3.0 kg of powder of a titanium zeolite were mixed in a pan mill with 2.5 kg of Ludox® AS 40, 3.83 kg of a 33.5% strength polystyrene dispersion, 120 g of Walocel®, 40 g of polyethylene oxide and 1000 g of water for 65 minutes. The mixture was subsequently extruded at a pressure of 140 bar to give 1.5 mm extrudates. The extrudates were dried at 120° C. for 16 hours and subsequently calcined in air at 490° C. for 5 hours. This gave 3.75 kg of extrudates having a Ti content of 1.5% and an Si content of 44.0%.

Preparation of the Polyester Alcohols

COMPARATIVE EXAMPLE 1

6040.1 g of adipic acid, 1406.8 g of ethylene glycol, 2042.6 g of 1,4-butanediol, 1 ppm of titanium tetrabutoxide and 5 ppm of tin octoate were placed in a round-bottom flask having a volume of 12 liters. The mixture was heated to 180° C. while stirring and kept at this temperature for 3 hours. The water formed was removed by distillation.

The mixture was then heated to 240° C. and kept at this temperature under a reduced pressure of 40 mbar until an acid number of less than 1 mg KOH/g had been reached.

The colorless, liquid polyester alcohol formed had the following characteristic properties:

| | |
|---|---|
| Hydroxyl number: | 56.5 mg KOH/g |
| Acid number: | 0.10 mg KOH/g |
| Viscosity: | 670 mPa.s at 75° C. |
| Water content: | 0.04% |
| Color number: | 64 APHA/Hazen |
| Cycle time: | 14 hours |
| Metal content of the polyester alcohol: | Ti: 0.21 ppm; Sn: 1.2 ppm |

COMPARATIVE EXAMPLE 2

5301.6 g of adipic acid, 1586.4 g of 1,6-hexanediol, 2419.5 g of 1,4-butanediol and 10 ppm of tin octoate were placed in a round-bottom flask having a volume of 12 liters. The mixture was heated to 180° C. while stirring and kept at this temperature for 3 hours. The water formed was removed by distillation.

The mixture was then heated to 240° C. and kept at this temperature under a reduced pressure of 40 mbar until an acid number of less than 1 mg KOH/g had been reached.

The colorless, liquid polyester alcohol formed had the following characteristic properties:

| | |
|---|---|
| Hydroxyl number: | 56 mg KOH/g |
| Acid number: | 0.27 mg KOH/g |
| Viscosity: | 690 mPa.s at 75° C. |
| Water content: | 0.1% |
| Color number: | 50 APHA/Hazen |
| Cycle time: | 11 hours |
| Metal content of the polyester alcohol: | Sn: 2.6 ppm |

EXAMPLE 1

6040.1 g of adipic acid, 1406.8 g of ethylene glycol, 2042.6 g of 1,4-butanediol and 18.9 g of titanium zeolite catalyst were placed in a round-bottom flask having a volume of 12 liters. The mixture was heated to 180° C. while stirring and kept at this temperature for 3 hours. The water formed was removed by distillation.

The mixture was then heated to 240° C. and kept at this temperature under a reduced pressure of 40 mbar until an acid number of less than 1 mg KOH/g had been reached.

Removal of the titanium zeolite catalyst by filtration gave a colorless, liquid polyester alcohol having the following characteristic properties:

| | |
|---|---|
| Hydroxyl number: | 57 mg KOH/g |
| Acid number: | 0.1 mg KOH/g |
| Viscosity: | 660 mPa.s at 75° C. |
| Water content: | 0.05% |
| Color number: | 12 APHA/Hazen |
| Cycle time: | 10 hours |
| Metal content of the polyester alcohol: | Ti: <0.1 ppm |

EXAMPLE 2

5301.6 g of adipic acid, 1586.4 g of 1,6-hexanediol, 2419.5 g of 1,4-butanediol and 18.6 g of titanium zeolite catalyst were placed in a round-bottom flask having a volume of 12 liters. The mixture was heated to 180° C. while stirring and kept at this temperature for 3 hours. The water formed was removed by distillation.

The mixture was then heated to 240° C. and kept at this temperature under a reduced pressure of 40 mbar until an acid number of less than 1 mg KOH/g had been reached.

Removal of the titanium zeolite catalyst by filtration gave a colorless, liquid polyester alcohol having the following characteristic properties:

| | |
|---|---|
| Hydroxyl number: | 56 mg KOH/g |
| Acid number: | 0.51 mg KOH/g |
| Viscosity: | 680 mPa.s at 75° C. |
| Water content: | 0.04% |
| Color number: | 18 APHA/Hazen |
| Cycle time: | 9 hours |
| Metal content of the polyester alcohol: | Ti: <0.1 ppm |

| Polyesterol | Diol | OH number (mg KOH/g) | Acid number (mg KOH/g) | Viscosity (75° C.) (mPa · s) | Color number (APHA/Hazen) | Cycle time hours |
|---|---|---|---|---|---|---|
| Comparative example 1 | Ethylene glycol, 1,4-butanediol | 56.5 | 0.1 | 670 | 64 | 14 |
| Comparative example 2 | 1,4-butanediol, 1,6-hexanediol | 56 | 0.27 | 690 | 50 | 11 |
| Example 1 | Ethylene glycol, 1,4-butanediol | 57 | 0.1 | 660 | 12 | 10 |
| Example 2 | 1,4-butanediol, 1,6-hexanediol | 56 | 0.51 | 680 | 18 | 9 |

Table 1 shows that the polyesterols prepared by the process of the invention could be prepared in a shorter cycle time and that the polyesterols prepared by the process of the invention have lower discoloration.

The invention claimed is:

1. A process for preparing polyester alcohols, comprising catalytically reacting at least one polyfunctional carboxylic acid with at least one polyfunctional alcohol, in the presence of a titanium zeolite catalyst, to obtain a polyester alcohol, wherein the titanium zeolite catalyst is in a form of a fixed bed.

2. The process according to claim 1, wherein the titanium zeolite catalyst has a structure selected from the group consisting of a MFI structure, a MOR structure, a BEA structure, a MWW structure, a RRO structure, a LEV structure, a FER structure, a MEL structure, and a MFI/MEL mixed structure.

3. The process according to claim 1, wherein the titanium zeolite catalyst has a structure selected from the group consisting of a MFI structure, a MEL structure and a MFI/MEL mixed structure.

4. The process according to claim 1, wherein the reacting is performed in its entirety in the presence of the titanium zeolite catalyst.

* * * * *